United States Patent
Ligozat et al.

(10) Patent No.: US 7,916,200 B2
(45) Date of Patent: Mar. 29, 2011

(54) IMAGE SENSOR WITH CORNER CUTS (75) Inventors: Thierry Ligozat, Grenoble (FR);
Grégoire Chenebaux, Grenoble (FR)

(73) Assignee: E2V Semiconductors (FR)

( * ) Notice: Subject to any disclaimer, the term of this patent is extended or adjusted under 35 U.S.C. 154(b) by 296 days.

(21) Appl. No.: 11/994,403

(22) PCT Filed: Jun. 15, 2006

(86) PCT No.: PCT/EP2006/063251
§ 371 (c)(1),
(2), (4) Date: Jul. 9, 2008

(87) PCT Pub. No.: WO2007/003495
PCT Pub. Date: Jan. 11, 2007

(65) Prior Publication Data
US 2009/0033777 A1    Feb. 5, 2009

(30) Foreign Application Priority Data
Jul. 1, 2005 (FR) ..................................... 05 07035

(51) Int. Cl.
H04N 3/14 (2006.01)
H04N 5/335 (2006.01)
(52) U.S. Cl. ..................................................... 348/315
(58) Field of Classification Search .......... 348/294–324, 348/315; 250/208.1; 257/291–294
See application file for complete search history.

(56) References Cited

U.S. PATENT DOCUMENTS

| 5,291,010 | A |   | 3/1994  | Tsuji |
|-----------|---|---|---------|-------|
| 5,510,623 | A | * | 4/1996  | Sayag et al. ............. 250/370.11 |
| 6,153,874 | A | * | 11/2000 | Monoi ....................... 250/208.1 |
| 6,794,654 | B1|   | 9/2004  | Hansen et al. |
| 7,262,399 | B2| * | 8/2007  | Hayashi et al. ............ 250/208.1 |
| 7,276,683 | B2| * | 10/2007 | Mori et al. ................. 250/208.1 |
| 2002/0021786 | A1 | * | 2/2002 | Hamamoto et al. ..... 250/370.11 |

FOREIGN PATENT DOCUMENTS

| EP | 1255401 A1 | 11/2002 |
| FR | 2857160    | 1/2005  |
| FR | 2857160 A1 | 1/2005  |

* cited by examiner

Primary Examiner — Sinh Tran
Assistant Examiner — Jason A Flohre
(74) Attorney, Agent, or Firm — Lowe Hauptman Ham & Berner, LLP (57) ABSTRACT

The invention relates to image sensors using a chip with cut corners. The sensor comprises a chip with cut corners comprising a matrix (10) of horizontal lines and vertical columns of photosensitive members, the matrix having a generally rectangular shape of horizontal width W and having four bevels, the sensor comprising as many current or voltage read blocks as there are matrix columns, in order to read the image signals detected by the photosensitive members, characterized in that the current or voltage read blocks are placed in a row (30, 30') along a horizontal edge of the matrix of width W' and are all housed within a vertical strip, the width W1 of which is substantially less than the maximum width W of the matrix. There are two superposed rows of current read blocks with blocks distributed at the same pitch as the pixel columns, or there is a single row with read blocks distributed with a pitch less than that of the pixel columns. The invention can be applied to CMOS technology intraoral radiological sensors.

19 Claims, 6 Drawing Sheets

IMAGE SENSOR WITH CORNER CUTS

CROSS-REFERENCE TO RELATED APPLICATIONS

The present Application is based on International Application No. PCT/EP2006/063251 filed on Jun. 15, 2006, which in turn corresponds to French Application No. 05 07035 filed on Jul. 1, 2005, and priority is hereby claimed under 35 USC §119 based on these applications. Each of these applications are hereby incorporated by reference in their entirety into the present application.

FIELD OF THE INVENTION

The invention relates to image sensors intended to be accommodated in areas where available space is reduced, and for which the aim, nevertheless, is to have an image capture area that is as large as possible. This is the case, for example, for dental radiological image sensors: they must be accommodated in the mouth of a patient and the size of the image taken must correspond at least to the height of a tooth and the width of several teeth. The space constraints are therefore considerable and it is necessary to try to save as much as possible with regard to the volume of the sensor with a given image surface. Furthermore, the need for patient comfort entails additional ergonomic constraints.

BACKGROUND OF THE INVENTION

Figure 1:
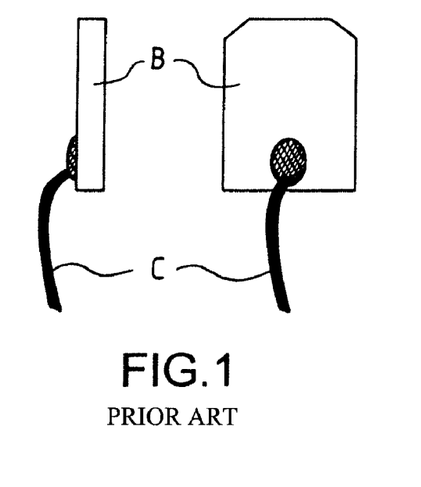
FIGS. 1 to 3, which have already been described, show known image sensor structures.

The radiological image sensor normally comprises a semiconductor chip having a matrix of photosensitive members and linked electronic circuits, a printed circuit board on which the chip and possibly some other components are mounted, a scintallator covering the chip, and occasionally a fiber-optic plate inserted between the scintillator and the chip. The unit is contained in a resin package B (FIG. 1) from which a connection cable C may extend to a system for processing the collected images (except in the case of wireless transmission, in which case a battery is provided, as a rule, in the package). The package conforms as closely as possible to the shape of the chip so as not to create unnecessary bulk.

The shape of the chip which is, a priori, rectangular requires the package to have a rectangular shape, which is neither ergonomic nor comfortable for the patient.

Figure 2:
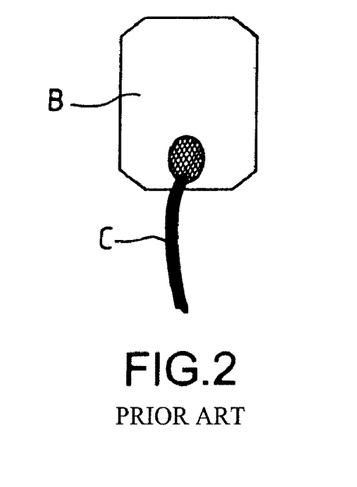

To improve the ergonomics and comfort in radiological image sensors which are made using CCD ("Charge Coupled Devices") technology, it has already been proposed to cut the corners of the package or make them round. To prevent losing image capture surface, it has been proposed in this case to use a chip which itself has cut corners. Sensors with chips having two cut corners (the two corners located at the front in the direction in which the sensor is inserted into the mouth) have been proposed (FIG. 1); sensors with four cut corners have also been proposed (FIG. 2). This results in structure adjustments such as, for example, the installation of a charge reading register in the middle of the chip rather than on the edges. These adjustments are possible in CCD technologies. They are not possible in CMOS technologies, i.e. technologies in which the photosensitive members have active members made from MOS transistors at each pixel in order to convert the photogenerated charges into voltage or current, and in which the current or voltage signals corresponding to each pixel are transmitted on a column conductor linked with each column of pixels.

Indeed, these technologies do not use a charge transfer register and reading systems could not be placed right in the middle of the chip without neutralizing an extremely large image area, and this is not acceptable.

However, CMOS technologies are extremely beneficial since they allow easy production, on a single integrated circuit chip, of both an image acquisition matrix and linked electronic circuits (control circuits, image signal collection circuits, image processing circuits, etc.). Moreover, these are technologies that consume less energy, which is advantageous.

This is why there is a need to combine the advantages of CMOS technology and the ergonomic shape of chips having cut corners.

There is however one considerable difficulty in carrying out this combination. This difficulty can be seen by referring first to FIG. 3 which schematically depicts a rectangular image sensor chip. The majority of the surface is taken up by a matrix 10 of lines and columns of photosensitive active members.

Figure 3:
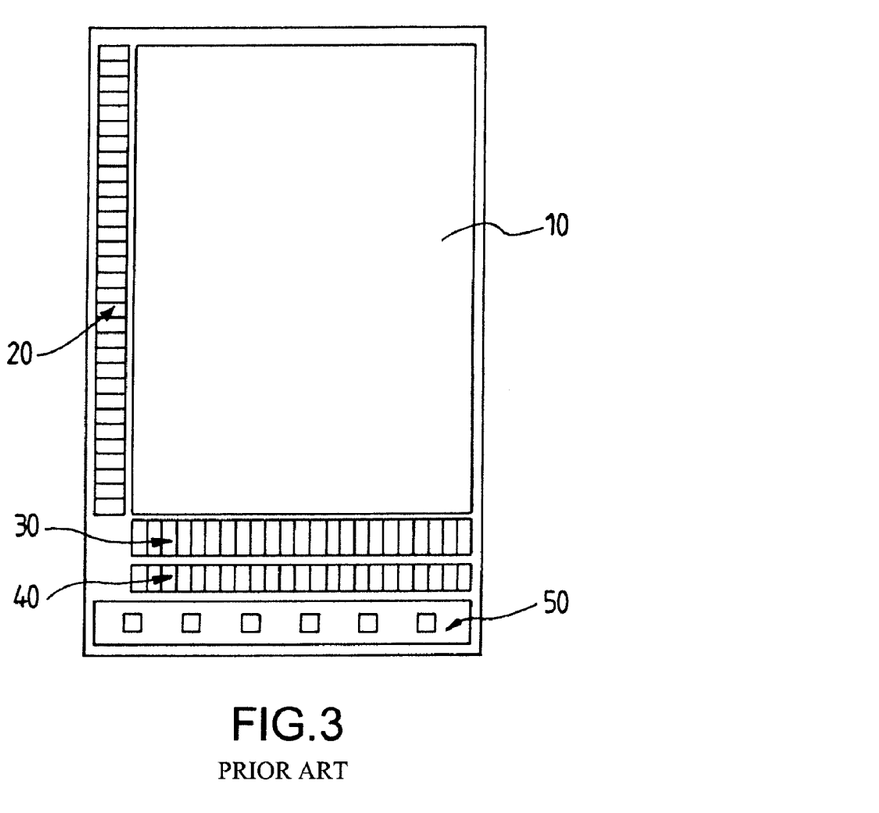

In practice, the matrix includes, for each line of pixels, one or more line conductors connecting all of the pixels of a same line, and for each column of pixels, a column conductor connecting all of the pixels of one and the same column.

The operation of such a CMOS technology matrix requires
a line select circuit, 20, to successively designate each line during an image reading operation; this is a purely digital circuit; it includes a line select block opposite each line;
a read circuit 30 for reading currents or voltages present on the column conductors during the addressing of a determined line, including, in principle, a circuit for storing these voltages or currents in order to store the image signals corresponding to the addressed line for the duration of the individual reading of all of the stored signals corresponding to this line; the signals which are coming from the pixels of this line and which are stored are indeed read sequentially on an output conductor of the matrix (not shown) to which the various current or voltage read blocks of the circuit 30 (one block per column) are connected; the read circuit 30 is a hybrid analog/digital circuit;
a column select circuit 40 for successively designating each column during an operation for reading a line that has just been stored; the designation of a column allows the stored signal corresponding to this column to be transmitted to the output of the matrix; the column select circuit is a digital circuit; it includes a select block linked with each read block, and therefore linked with each column; this circuit 40 is not necessarily present, in particular when the image sensor comprises a high-speed analog-to-digital converter at the output of the read circuit 30;
various electronic circuits and input/output pads of the chip, the assembly being housed in a space given the general reference 50; these circuits can notably include a sequencer for the successive addressing of the lines and then the columns for a given line.

The read and select circuits are placed at the periphery of the matrix, opposite the lines on the one hand, and the columns on the other. The line select circuit 20 extends along a vertical edge of the matrix, parallel to the columns, with a block opposite each line; it can be split and can extend along the two vertical edges. The reading (and storage) circuit 30 extends, for example, along the horizontal lower edge of the matrix. The column select circuit 40 also extends along the horizontal lower edge, below the read circuit 30. The space 50 extends below the circuit 40. More precisely, the line select circuit 20 includes a multi-conductor address bus (not shown)

which extends along the entirety of a vertical edge of the matrix, parallel to the columns, and a select block opposite each line. The inputs of the select block are the bus conductors and the outputs are one or more line conductors which horizontally connect all of the pixels of the line corresponding to the elementary block.

The storage and current or voltage read circuit 30 includes, for each column, an elementary read block which carries out the reading and storage function; this block is positioned opposite this column, and it receives, as an input, the column conductor corresponding to this column. This block can comprise a buffer amplifier, one or more associated capacitors, and switches; it acts as a sample-and-hold circuit, i.e. in a first phase it samples a current or voltage value present on the column conductor, and in a second phase, it stores the sampled voltage until its content is read (sequential reading, block by block).

The column select circuit 40 includes an address bus (not shown) formed of several conductors, which extends along a horizontal edge of the matrix, parallel to the lines, and a column select block opposite each column; this select block is a decoding circuit (but could be a simple shift register) whose inputs are the conductors of this address bus and whose output is a signal for controlling a switch inserted between the current or voltage read block linked with the corresponding column and the output conductor of the matrix. The address bus selects an elementary block and connects, to the output conductor, the output of the sample-and-hold circuit linked with the designated column. The output conductor successively provides the image signals corresponding to each pixel of the matrix, line by line and pixel by pixel in the line.

Thus, for a line addressed by the line address bus, the signals of all of the pixels of the line are stored in the read blocks 30 located at the bottom of the matrix, then they are successively transmitted to the output under the control of the column address bus, before a new line is addressed.

Figure 4:
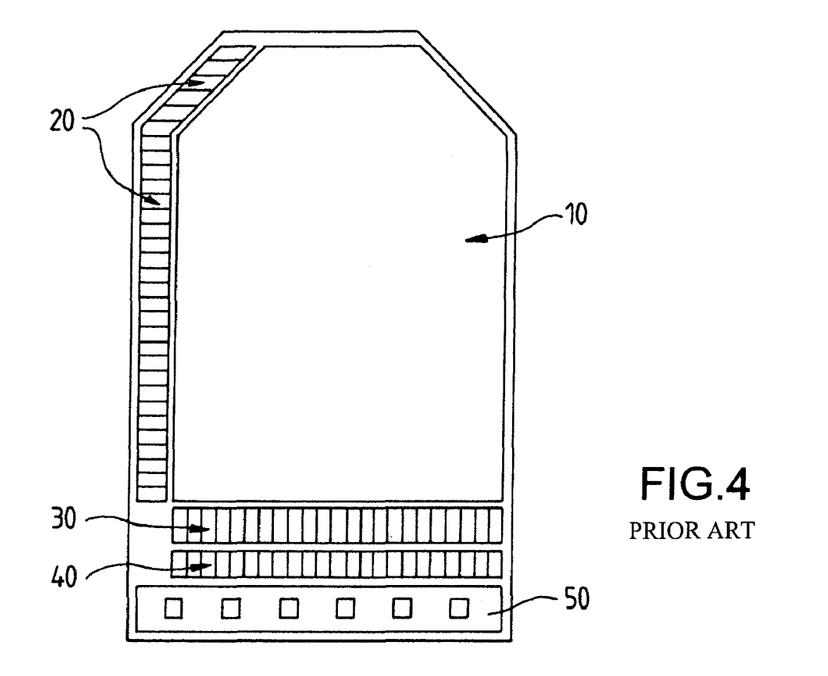
FIG. 4 shows a circuit general arrangement which is possible for a sensor with two cut corners.

If a matrix with two or four cut corners is now used instead of the rectangular matrix of FIG. 3, the line select circuit extends partially along the oblique edges making up the bevels of the matrix in order to remain opposite each line of the matrix while being housed in the narrow residual space between the edge of the matrix and the edge of the chip. This, in itself, does not cause a particular problem. FIG. 4 shows the general arrangement for a matrix with two cut corners.

However, in the case of a matrix with four cut corners, the column select circuit and the current or voltage read circuit must also extend partially along the cut corners in order to remain opposite the columns that terminate on these corners. It has been noted that this arrangement can generate a fixed pattern noise (FPN). Indeed, the nonuniform position and production of analog circuits creates small gain differences which are found in the image in the form of fixed pattern noise: the individual read circuits should all be absolutely identical, but they are not in reality. There is a factor of dependence between the gain of an amplifier for example and the position of the amplifier in the chip. In the case where amplifiers are located on a single line, it is quite easy to correct the effect of this dependence along a geometrical axis. In the case where they are located both on a horizontal line (dependence along one axis) and on an oblique line (dependence along two axes), this correction is a lot more difficult and there is a risk that fixed noise linked to the structure (and not only to technological imperfections) will remain in spite of the corrections.

Moreover, on the oblique corners of the matrix, it is not possible to have, as is the case with a rectangular matrix, the line select blocks along a horizontal edge and the read blocks along a vertical edge. The two series are placed along one and the same oblique edge. A choice must therefore be made as to whether to position the line select blocks in immediate proximity to the lines or the read blocks in immediate proximity to the columns, but it is not possible have both at the same time. Yet, in both cases, this requires line address signals to be passed above the read blocks. These signals are digital signals of large amplitude which exert a virtually unacceptable capacitive effect on the read blocks which are extremely sensitive to capacitive effects (these are analog circuits for measuring extremely small currents and voltages). It would therefore be necessary to insert shielding layers between the lines transporting digital signals and the read blocks; this is difficult to do given the limited number of conductive levels available at the location of the read blocks (these blocks, in principle, use all of the conductive levels that the technology used makes available).

Figure 5:
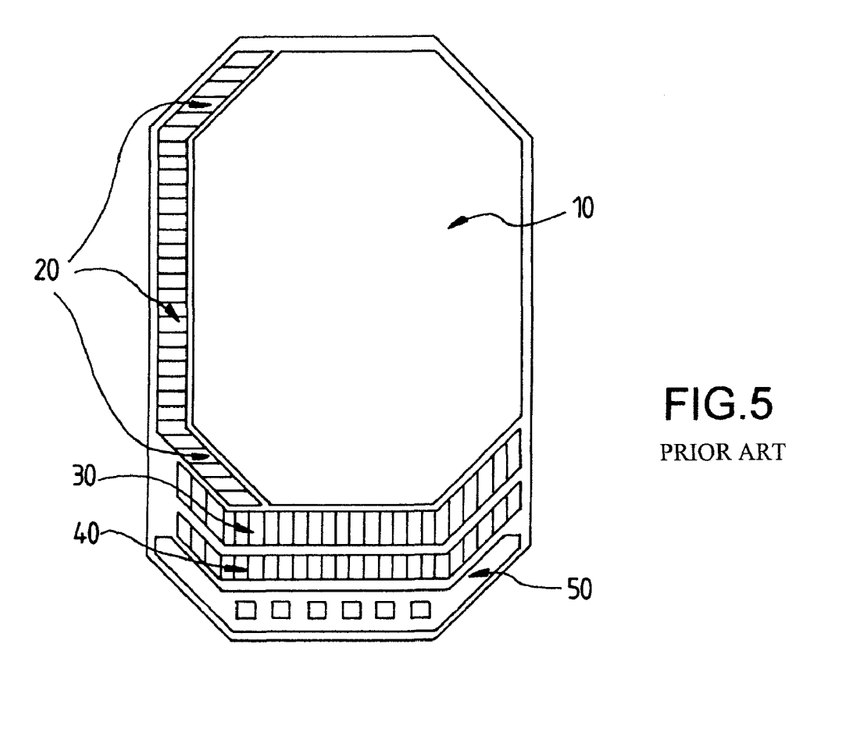
FIGS. 5 and 6 show general arrangements that are possible for sensors with four cut corners.
Figure 6:
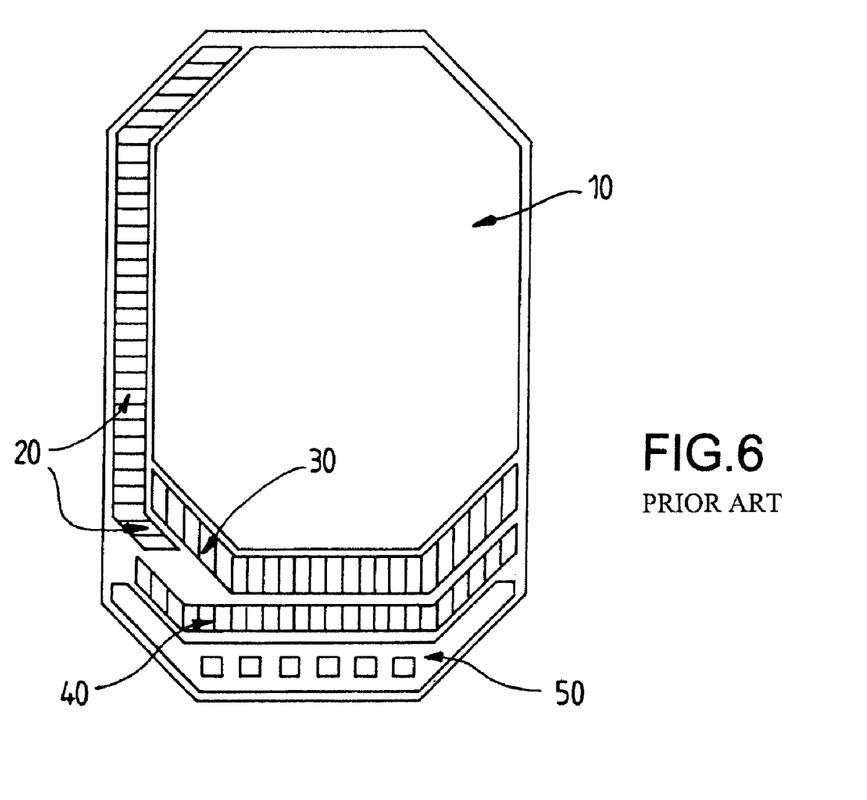

FIGS. 5 and 6 show two examples of structures illustrating the possible positions of the select and read circuits in a matrix with four cut corners: line select blocks 20 in immediate proximity to the bevel of the matrix in FIG. 5, and current or voltage read blocks 30 in immediate proximity to the bevel in FIG. 6.

To solve the difficulties linked with these structures, the invention proposes an image sensor having a chip with cut corners, comprising a matrix of horizontal lines and vertical columns of photosensitive members, the matrix having a generally rectangular shape of horizontal width L and having four bevels, the sensor comprising as many current or voltage read blocks as there are matrix columns, in order to read the image signals detected by the photosensitive members of a column and transmitted by a column conductor linked with this column, characterized in that the current or voltage read blocks are placed along a horizontal edge of the matrix and are all housed within a vertical strip, the width L1 of which is substantially less than the maximum width L of the matrix.

In practice, if L' is the width at the bottom of the matrix, i.e. the narrow horizontal width which remains between the bevels at the bottom of the matrix (on the side where the current or voltage read blocks are located), all of the blocks would be fitted into the width L' or into a width which is more or less equal to the width L'.

If the sensor comprises column select blocks linked with the read blocks, these column select blocks would be all housed in the same width L1.

SUMMARY OF THE INVENTION

In a first embodiment, the read blocks are all placed with the same pitch (preferably the pitch of the columns with which they are linked), and the blocks which are linked with the columns terminating along the bevels are located below blocks linked with columns terminating along the horizontal edge of the matrix. The read blocks are placed in two rows, one located below the other.

In a second embodiment, the read blocks are placed along a horizontal edge of the matrix with a pitch between blocks which is smaller than the pitch of the columns with which they are linked. All of the read blocks are housed in a single row, in a width L1 which is substantially less than the maximum width of the matrix. The ratio between the pitch of the read blocks and the pitch of the pixels is preferably more or less equal to L'/L, such that the blocks fit mainly in the width L' of the bottom of the matrix.

Still other advantages of embodiments according to the present invention will become readily apparent to those skilled in the art from the following detailed description, wherein the preferred embodiments of the invention are shown and described, simply by way of illustration of the best mode contemplated of carrying out the invention. As will be realized, the invention is capable of other and different embodiments, and its several details are capable of modifications in various obvious respects, all without departing from the invention.

BRIEF DESCRIPTION OF THE DRAWINGS

The present invention is illustrated by way of example, and not by limitation, in the figures of the accompanying drawings, wherein elements having the same reference numeral designations represent like elements throughout and wherein.

DETAILED DESCRIPTION OF THE DRAWINGS

Figure 7:
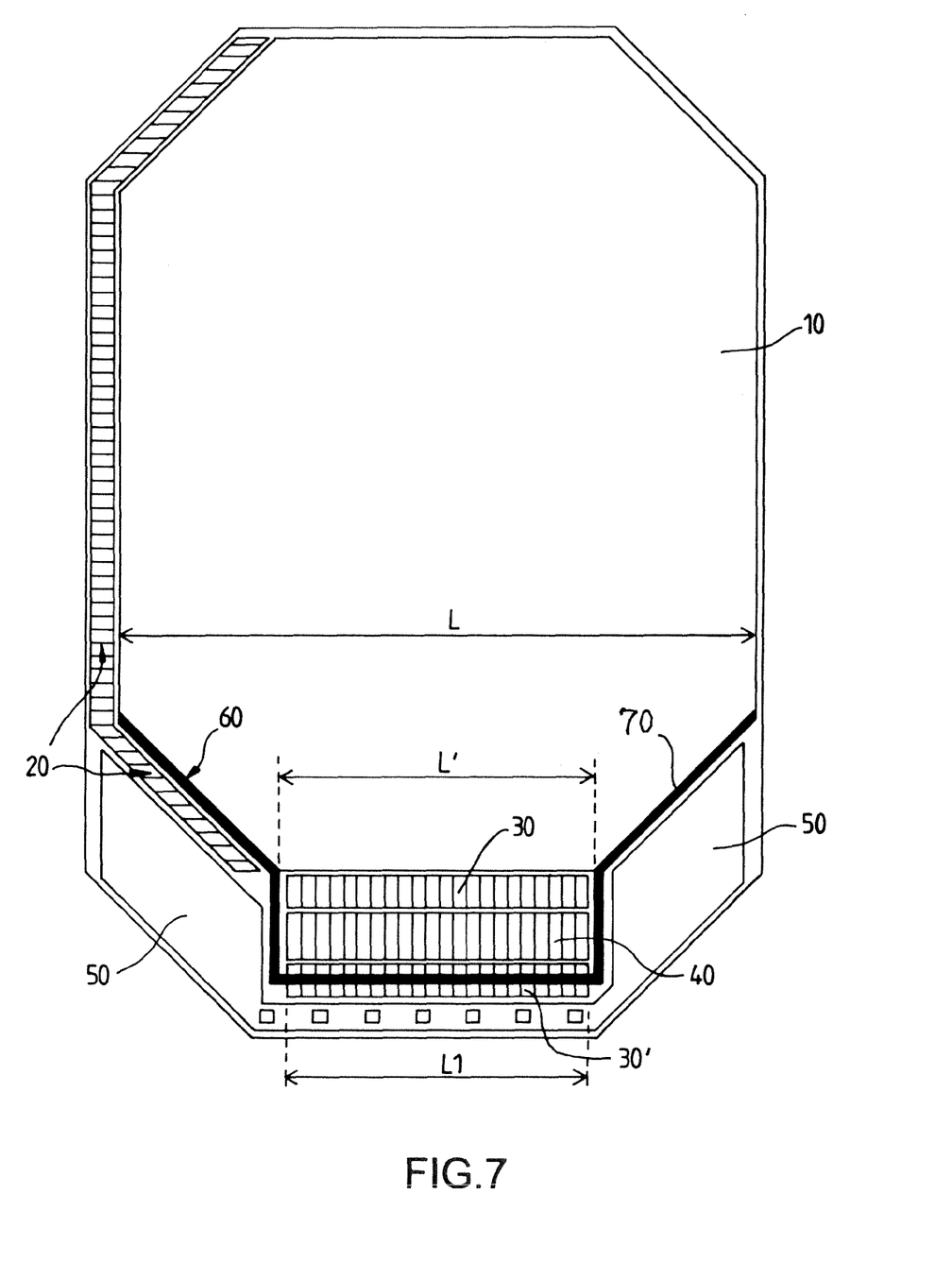
FIG. 7 shows a sensor according to the invention in a first embodiment.

The general arrangement of the circuits of the sensor according to the invention is shown in FIG. 7. The references which are identical to those of the preceding figures correspond to members having the same functions.

The matrix 10 has four cut corners; the corners are cut in principle at 45° and are cut over a substantial part of the matrix. For example, if the matrix comprises N columns in total in the largest width thereof and N' columns at the horizontal base thereof, it can be envisaged that N' is practically half of N, which means that the cut corners each extend over approximately one quarter of the columns of the matrix.

L is taken to mean the total width of the matrix and L' the width of the horizontal base (the term horizontal corresponds to the direction parallel to the addressing lines, the term vertical corresponds to the direction parallel to the columns which provide the collected signals). L' can therefore be equal to approximately L/2.

The line select circuits 20 extend both along a vertical edge of the matrix and along the oblique edges adjacent this vertical edge. They are shown in the form of a series of rectangles and parallelograms which are juxtaposed above each other, each rectangle (along the vertical edge) or parallelogram (along the oblique edges) corresponding to a block for selecting a respective line of the matrix and being opposite this line. For purposes of symmetry, the line select circuits may also extend over the other vertical edge and the other two oblique edges. The symmetry is in relation to a vertical center line which cuts the matrix in two. This arrangement is optional. It is useful for reasons of centering, redundancy and reduction of the access time to the center pixels of the matrix. It is not shown.

According to the invention, the current or voltage read circuit is made up of a series of individual blocks (one block per matrix column) which are placed side-by-side in one or two horizontal rows, within a width L1, measured in the horizontal direction, which is clearly shorter than the width L of the matrix, and which is preferably close to the width L' of the horizontal base of the matrix. The individual blocks are represented by juxtaposed rectangles each corresponding to a respective column.

In FIG. 7, the read blocks are placed in two horizontal rows 30 and 30' and inside a vertical strip of width L1.

All of the individual read blocks linked with the columns which lead to the horizontal base of the matrix are placed in a first row 30 immediately under this base, one block being located below each column, and the distribution pitch of the blocks is the same as the distribution pitch of the columns, i.e. the same as the pitch of the pixels of the matrix in the horizontal direction. All of the other read blocks, which are therefore linked with the columns which lead onto the bevels of the matrix, are placed in a second horizontal row 30' below the blocks of the first row and with the same pitch. The blocks of the two rows are preferably identical with each other; they may however be placed symmetrical with those of the first row (symmetry in relation to a horizontal line).

If there is a column select circuit 40 (in the general case), it is located between the two read block rows 30 and 30'.

The column conductors coming from the columns terminating on one of the bevels (the left bevel in the figure) are grouped together in a multi-conductor bus 60 (there are as many conductors as there are columns terminating on the bevel) which extends along this bevel and then runs vertically alongside the row 30 and the column select circuit 40, as far as the read blocks of the left half of the second row 30'. This bus is preferably inserted between the line decoding blocks 20 located along the bevels and the oblique edge of the matrix. The line selection conductors in this case cross the column conductor bus, and a shield conductive layer, brought to a fixed potential, is preferably inserted between the line conductors and the column conductors at the point where they cross so as to prevent the digital signals applied to the lines from exerting a capacitive effect on the analog potentials of the column conductors, which would interfere with reading. These crossings take place where there are no read blocks; as a result, it is easy to achieve them technologically with only two conductor levels and an insulating level therebetween.

On the other side of the matrix, on the right bevel, the column conductors are grouped together in another multi-conductor bus 70. This bus 70 runs alongside the bevel then runs down along the circuits 30 and 40 to join the right half of the read block row 30'.

The area 50 which is used to house the input/output pads and other functional circuits extends to the bottom of the chip, both under the horizontal lower edge of the matrix and under the oblique edges, so as to optimize the fill rate.

The current or voltage read blocks (30, 30') are placed parallel to each other and do not generate any significant and uncontrollable fixed pattern noise (FPN) which would be linked to the two-dimensional structure. As regards the line select circuits (20), they only handle binary data and are therefore not sensitive to the fixed noise linked to the two-dimensional structure, which would result from their positions in a vertical column and along bevels.

The block 30' does not necessarily take up all of the width L1 of the horizontal base of the matrix.

Figure 8:
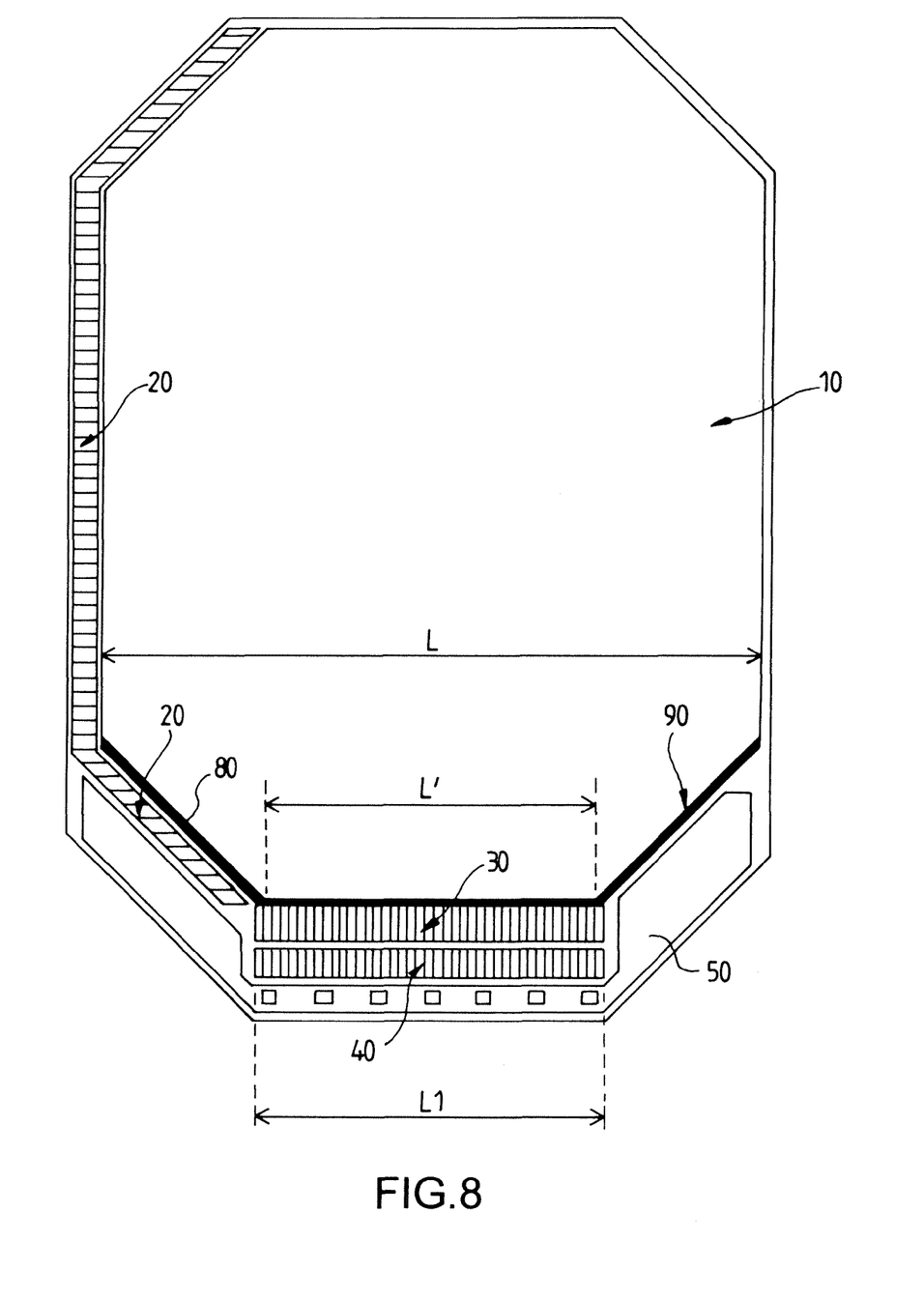
FIG. 8 shows a sensor according to the invention in a second embodiment.

FIG. 8 shows another embodiment in which all of the read blocks are placed side-by-side in a single horizontal row 30, within a width L1 which is less than L and which is preferably more or less the width L' of the horizontal base of the matrix. The blocks are juxtaposed with a pitch that is smaller than the pitch of the columns of the matrix, i.e. smaller than the pitch of the pixels of a line. The pitch is in a L1/L ratio (in practice approximately L'/L, and for example ½ if L'=L/2) with the pitch of the pixel columns such that all of the read blocks fit in the width L1. If the pitch of the columns is approximately 10 micrometers, it is easy to fit a current or voltage read block having a few transistors into a pitch of 5 micrometers.

If there is a column select circuit 40, it is located under the read block row 30 and the column select blocks are at the same pitch as the read blocks.

A column conductor bus 80 (on the left) and a column conductor bus 90 (on the right) extends along a respective oblique edge (between the matrix and the line decoders for the left bus 80) and along the horizontal lower edge of the matrix (between the matrix and the read blocks). They bring each of the column conductors, whether coming from a left or right bevel or from the lower edge of the matrix, to a corresponding read block of the single row 30. These buses are necessary since the read blocks are not located below the pixel columns of the matrix, even for the columns which run down to the horizontal edge, since the pitch of the read blocks is not the same as the pitch of the pixel columns of the matrix; only one or two center columns of the matrix end above the corresponding blocks.

Figure 9:
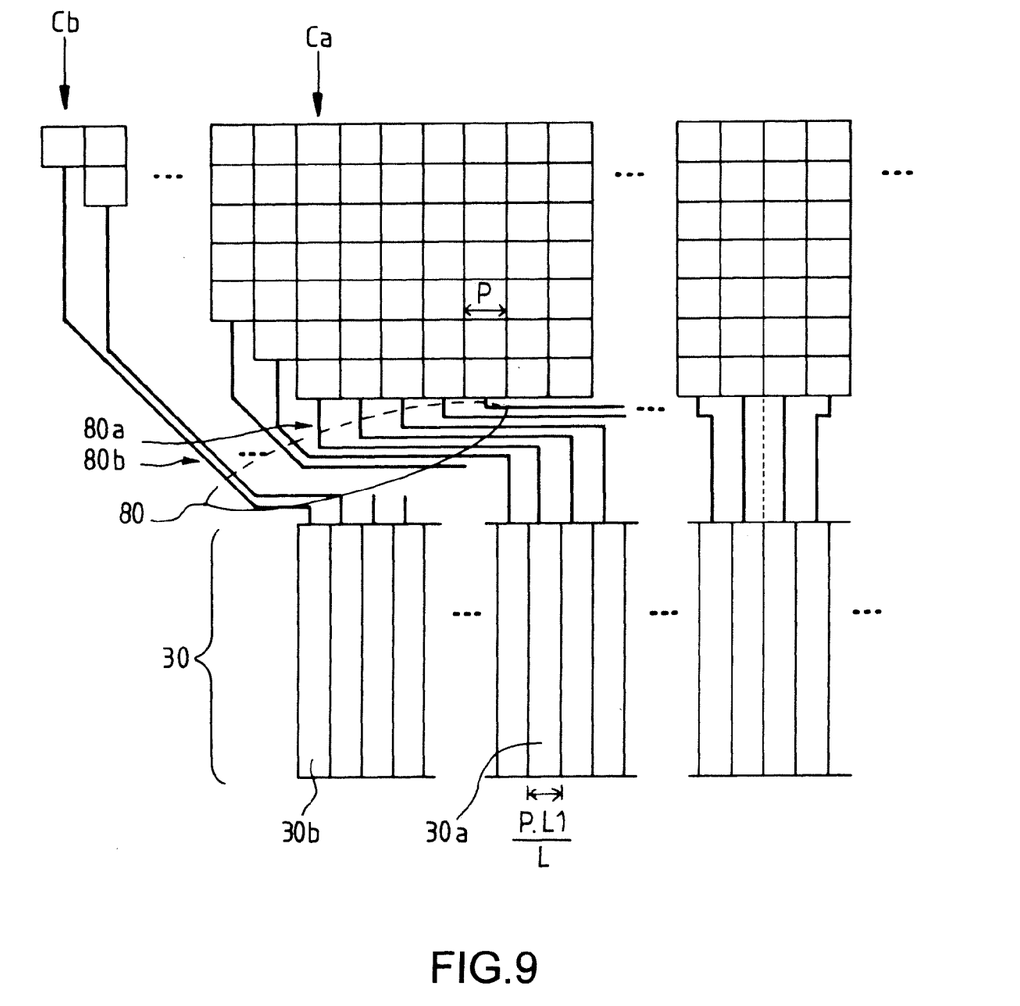
FIG. 9 shows a structural detail of the embodiment of FIG. 8.

FIG. 9 shows an enlarged view of the arrangement of FIG. 8, in order to explain more clearly the structure of the conductor bus 80. It includes conductors such as 80a, coming from a column Ca terminating on the horizontal lower edge of the matrix, this conductor 80a extending to a read block 30a which is located under the horizontal lower edge of the matrix but which is not located opposite the column Ca. It also includes conductors such as 80b, coming from a column Cb terminating on an oblique edge, these conductors 80b extending to a read block 30b which is located under the horizontal lower edge of the matrix. The conductors 80 can be produced with one or more metallization levels, the use of several superposed levels reducing the width of the bus.

The pitch of the pixel columns is P. The pitch of the read blocks is P. (L1/L), which is smaller than P.

The invention can be applied in particular to intraoral dental radiological image sensors for which size and patient comfort are important parameters.

In this case, the chip can have dimensions of approximately 20 mm per side, for example a width L of 20 mm and a base width L' of 10 millimeters, i.e. approximately half.

It will be readily seen by one of ordinary skill in the art that embodiments according to the present invention fulfill many of the advantages set forth above. After reading the foregoing specification, one of ordinary skill will be able to affect various changes, substitutions of equivalents and various other aspects of the invention as broadly disclosed herein. It is therefore intended that the protection granted hereon be limited only by the definition contained in the appended claims and equivalents thereof.

The invention claimed is:

1. An image sensor having a rectangular integrated circuit chip with cut corners, comprising:
   a matrix of horizontal lines and vertical columns of photosensitive active pixels, each column of pixels having a respective column conductor extending along the column and electrically connectable to the pixels of the column, the matrix having a generally rectangular shape of horizontal width L and having four bevels, wherein the sensor comprises a line selection circuit for selecting a line of pixels and connecting the pixels of said line to said column conductors, and, for each column, a respective current or voltage read block connected to said respective column conductor in order to read image signals detected by a photosensitive pixel located at the intersection of said column and a selected line, wherein the current or voltage read blocks are placed in a row along a horizontal edge, of width L', of the matrix and are all housed within a vertical strip, the width L1 of which is substantially less than the maximum width L of the matrix.

2. The image sensor as claimed in claim 1, wherein the current or voltage read blocks are placed in a strip of width L1 which is substantially equal to the width L' of the horizontal edge of the matrix between the bevels of the matrix.

3. The image sensor as claimed in claim 1, wherein the read blocks are placed in two horizontal rows, one located below the other, the blocks which are linked with the columns terminating along the bevels being located below blocks linked with columns terminating along the horizontal edge of the matrix and the pitch of the blocks being the same in both rows.

4. The image sensor as claimed in claim 3, wherein the pitch of the read blocks is the same as that of the columns with which they are linked.

5. The image sensor as claimed in claim 3, wherein a conductor bus extends along a bevel in order to connect the column conductors terminating on this bevel to the second read block row.

6. The image sensor as claimed in claim 5, wherein the conductor bus extends along the bevel between the matrix and line select blocks used to select the image lines.

7. The image sensor as claimed in claim 3, comprising a column select block row which is positioned between the two read block rows, each column select block being used to select a read block linked with a respective column.

8. The image sensor as claimed in claim 1, wherein the current or voltage read blocks are placed along a horizontal edge of the matrix with a pitch between blocks which is smaller than the pitch of the columns with which they are linked, all of the read blocks being housed in a single row, in a width L1 which is substantially less than the maximum width of the matrix.

9. The image sensor as claimed in claim 8, wherein a conductor bus extends along a bevel and the horizontal edge of the matrix in order to connect the column conductors terminating on this bevel and on the horizontal edge to the read blocks.

10. The image sensor as claimed in claim 9, wherein the conductor bus extends along the bevel between the matrix and line select blocks used to select the image lines.

11. The image sensor as claimed in claim 8, comprising a column select block row used to select the current or voltage read blocks, this row being positioned below the read block row and the column select blocks being at the same pitch as the current or voltage read blocks.

12. The image sensor as claimed in claim 1, wherein the image sensor makes up an intraoral dental radiological image sensor.

13. The image sensor as claimed in claim 2, comprising a column select block row which is positioned between the two read block rows, each column select block being used to select a read block linked with a respective column.

14. The image sensor as claimed in claim 4, comprising a column select block row which is positioned between the two read block rows, each column select block being used to select a read block linked with a respective column.

15. The image sensor as claimed in claim 5, comprising a column select block row which is positioned between the two read block rows, each column select block being used to select a read block linked with a respective column.

16. The image sensor as claimed in claim 6, comprising a column select block row which is positioned between the two read block rows, each column select block being used to select a read block linked with a respective column.

17. The image sensor as claimed in claim 2, wherein the current or voltage read blocks are placed along a horizontal edge of the matrix with a pitch between blocks which is smaller than the pitch of the columns with which they are linked, all of the read blocks being housed in a single row, in a width L1 which is substantially less than the maximum width L of the matrix.

18. The image sensor as claimed in claim 9, comprising a column select block row used to select the current or voltage read blocks, this row being positioned below the read block row and the column select blocks being at the same pitch as the current or voltage read blocks.

19. The image sensor as claimed in claim 10, comprising a column select block row used to select the current or voltage read blocks, this row being positioned below the read block row and the column select blocks being at the same pitch as the current or voltage read blocks.

\* \* \* \* \*